United States Patent [19]

Lee

[11] Patent Number: 4,913,848
[45] Date of Patent: Apr. 3, 1990

[54] PROCESS FOR PRODUCING A HIGH PURITY DIBROMONEOPENTYL GLYCOL PRODUCT

[75] Inventor: John Y. Lee, Baton Rouge, La.

[73] Assignee: Ethyl Corporation, Richmond, Calif.

[21] Appl. No.: 256,593

[22] Filed: Oct. 12, 1988

[51] Int. Cl.$^4$ .................... C09K 21/00; C07C 31/34; C07C 69/34; C07C 69/52
[52] U.S. Cl. .................................. 252/609; 252/601; 560/197; 560/264; 568/844
[58] Field of Search .................... 203/38, 58; 568/844; 252/601, 609; 560/197, 264

[56] References Cited

U.S. PATENT DOCUMENTS

| | | | |
|---|---|---|---|
| 3,876,509 | 4/1975 | Davis et al. | 203/38 |
| 3,883,581 | 5/1975 | Davis et al. | 203/38 |
| 3,891,605 | 6/1975 | Larsen et al. | 525/27 |
| 3,932,541 | 1/1976 | Davis et al. | 260/633 |
| 4,154,966 | 5/1979 | Weil | 568/844 |
| 4,378,440 | 3/1983 | Bertrand | 524/380 |
| 4,699,943 | 10/1987 | Bertrand | 524/388 |

Primary Examiner—Howard J. Locker
Attorney, Agent, or Firm—Edgar E. Spielman, Jr.

[57] ABSTRACT

This invention relates to a process for treating a first product which contains monobromopentaerythritol, dibromoneopentyl glycol and tribromoneopentyl alcohol to yield a second product having a dibromoneopentyl glycol content, on a weight percent basis, greater than that of the first product. The process features forming a stirrable mass from the first product and a solvent system in which, at a temperature within the range of from about 0° C. to about 40° C., the monobromopentaerythritol and the tribromoneopentyl alcohol are more soluble than the dibromoneopentyl glycol and in which at least 85% of the dibromoneopentyl glycol in the mass is insoluble; maintaining the reaction mass within the aforementioned temperature range to realize an insoluble portion and a solvent and solute portion; and separating the insoluble portion and the solvent and solute portion without substantial precipitation of the solute from the solvent and solute portion. The separated insoluble portion is the second product.

9 Claims, No Drawings

PROCESS FOR PRODUCING A HIGH PURITY DIBROMONEOPENTYL GLYCOL PRODUCT

BACKGROUND OF THE INVENTION

This invention relates to a process for treating the product obtained from the bromination of pentaerythritol to yield a product enriched in monobromopentaerythritol, dibromoneopentyl glycol or tribromoneopentyl alcohol.

Dibromoneopentyl glycol (DBNPG) is a commercial, reactive flame retardant having especially useful qualities in polyester- and polyurethane-based formulations. A commercial process for producing DBNPG is disclosed in U.S. Pat. No. 3,932,541. While this process produces a useful product, the product is generally only about 80+ wt % DBNPG, with the remainder being monobromopentaerythritol (MBP) and tribromoneopentyl alcohol (TBNPA). Such a DBNPG product has been used in some polyurethane-based formulations, but is not preferred for use in unsaturated polyesterbased formulations since the presence of more than a few percent of MBP and TBNPA is believed to cause color problems. Generally, the DBNPG product should contain at least about 95+ wt % DBNPG for the product to be suitable for use in unsaturated polyester formulations.

In view of these different requirements for DBNPG purity, it would be desirable if the lower purity product could be, when needed, upgraded to the higher purity product.

It is, therefore, an object of this invention to provide a process for enhancing the DBNPG purity of a composition which contains DBNPG, MBP and TBNPA. It is also an object of this invention to provide a process for effecting substantial separation of DBNPG, MBP and TBNPA from each other.

THE INVENTION

This invention relates to a process for treating a first product which contains monobromopentaerythritol, dibromoneopentyl glycol and tribromoneopentyl alcohol to yield a second product having a dibromoneopentyl glycol content, on a weight percent basis, greater than that of the first product. The process comprises: forming a stirrable mass from at least (i) the first product and (ii) a solvent system in which, at a temperature within the range of from about 0° C. to about 40° C., said monobromopentaerythritol and said tribromoneopentyl alcohol are more soluble than said dibromoneopentyl glycol, and in which at least 85% of the dibromoneopentyl glycol in the mass is insoluble; maintaining the reaction mass at a temperature within the above-stated range to form an insoluble portion and a solvent and solute portion; and separating the insoluble portion from the solvent and solute portion without the substantial precipitation of the solute from the solvent and solute portion. The separated insoluble portion is the desired second product. The weight percent basis for the dibromoneopentyl glycol in the first and second product is on the total weight, respectively, of the first and second products.

The first product can be any composition which contains MBP, DBNPG and TBNPA provided that the composition does not contain any constituent which would adversely effect the purposes of the process of this invention. Most commonly, the first product will be the product of a process for production of DBNPG, such as the process disclosed in U.S. Pat. No. 3,932,541. In most instances, the first product will be predominant in DBNPG, that is the first product will contain at least 50 wt % DBNPG, with the MBP and TBNPA being present in lesser amounts. However, it is to be understood that the first product can contain predominant amounts of MBP and/or TBNPA and that in such cases the process of this invention will still provide a product, i.e. the second product, which will have a greater DBNPG content than the first product. From a commercial standpoint, the process of this invention will generally be used to treat first products which contain 60-90 wt % DBNPG, 0-20 wt % MBP and 0-20 wt % TBNPA, based upon the total weight of the first product. It is most convenient that the first product be in a flaked or powdered form.

The solvent system can be comprised of one or more solvents. A solvent system which contains a first solvent in which the MBP is soluble and a second solvent in which TBNPA is soluble is preferred as most inexpensive single solvents do not easily dissolve both MBP and TBNPA while at the same time acting as a poor solvent for DBNPG. Exemplary solvents which may be used in the process of this invention are, for MBP, water, and for TBNPA, toluene, benzene, tetrachloroethylene, cyclohexane, trichloroethylene, dichlorobenzene, bromobenzene, methylene dibromide, methylene dichloride, xylenes, chlorobenzene, and carbon tetrachloride. When separation of the MBP from the TBNPA is desired, the MBP solvent and the TBNPA solvent should be, with their solutes, easily separable one from the other. From the standpoint of ease-of-separation, it is preferred that the MBP solvent and its solutes be immiscible with the TBNPA solvent and its solutes. A most highly preferred solvent system is one containing water as the MBP solvent and toluene as the TBNPA solvent.

The solvent system is used in an amount which will be sufficient to dissolve at least 85 wt % of the MBP and at least 85 wt % of the TBNPA initially present in the first product. Also, the amount of solvent system used should provide sufficient fluidity to the mass so that it can be easily mixed thereby insuring maximum opportunity for the MBP and the TBNPA to be dissolved into the solvent system. Generally, the amount of solvent system used should be above about 1 mL/g of the first product. Amounts far in excess of this minimum amount can be used, however, such amounts may not provide a benefit in DBNPG purity which is commensurate with the costs associated with such use. From an economical standpoint, the preferred amount of solvent system used can be within the range of from about 1 to about 5 mL/g of first product.

With regard to the preferred water and toluene solvent system, a preferred volumetric ratio of water to toluene is within the range of from about 0.1:1 to about 1:0.1. Also, the mass will have good mixability when the water and toluene are provided in an amount sufficient to give from about 1 to about 5 mL of solvent system per gram of first product.

After the mass has been formed, the mass is preferably held at a temperature within the range of from about 25° C. to about 75° C. for that period of time needed to achieve the practical maximum dissolution of the MBP and TBNPA. Some DBNPG will also be dissolved, but the major portion thereof will be recaptured by the subsequent cooling described below. Less time or cooler temperatures can be used but there will be more MBP and TBNPA in the second product than would otherwise be normally obtainable. Holding the temperature within the above range for at least 0.1 hour is preferred.

Subsequent to maintaining the mass within the above temperature range, the mass is cooled to a temperature within the range of from about 0° C. to about 40° C. to maximize recovery of DBNPG by precipitation. The insoluble portion is recovered from the other portion by any technique which does not cause substantial precipitation of the solutes from the solvent and solute portion. Preferred techniques are filtration and centrifugation.

In another embodiment, the process of this invention can also be used to recover a second product which contains, on a wt % basis, more MBP or TBNPA than that contained in a first product. Also, this embodiment can be used to separate and remove, from a first product, MBP, DBNPG and TBNPA. This process embodiment is run substantially as is the process described above except that the solvent system must contain two separate solvents, i.e., a MBP solvent and a TBNPA solvent, and these two solvents must be easily separable, e.g. immiscible in one another. The insoluble DBNPG product produced by this embodiment is recovered as before described. The MBP solvent and its MBP predominant solutes and the TBNPA solvent and its TBNPA predominant solutes, if immiscible in one another, will form layers upon standing. After the layers are formed they can be separated by conventional techniques, e.g., decantation, phase-cut, syphon, etc. After separation, each layer is heated to evaporate solvent and to precipitate out the respective MBP and TBNPA solutes, which solutes are then recovered by conventional techniques, e.g., further solvent extraction and/or recrystallization.

The following examples illustrate the process of this invention and are not to be considered as limiting the scope of the invention.

EXAMPLE I

Five grams of a material which contained 0.80 g (16 wt %) of MBP, 3.8 g (76 wt %) of DBNPG and 0.40 g (8 wt %) of TBNPA were fed to a 50-mL flask equipped with a stirring bar. To the flask was fed a solvent mixture containing 10 mL of toluene and 10 mL of water. The resultant slurry was stirred at a temperature of about 45° C. for 3 hrs and then cooled to 25° C. After cooling, solids in the mass were removed therefrom by filtration and dried. The solids weighed 3.65 g and contained 3.50 g (95.9 wt %) of DBNPG, 0.10 g (2.7 wt %) of MBP and 0.05 g (1.36 wt %) of TBNPA. This represents 92.1 wt % of the starting DBNPG, 12.5 wt % of the starting MBP and 12.5 wt % of the starting TBNPA. The separated water layer was found to contain 0.70 g (78 wt % of total MBP and DBNPG weight in the water layer) of MBP and 0.20 g (22 wt % of total MBP and DBNPG weight in the water layer) of DBNPG. This represents 87.5 wt % of the starting MBP and 5.2 wt % of the starting DBNPG. The toluene layer was found to contain 0.09 g (20.5 wt % of total DBNPG and TBNPA weight in the toluene layer) of DBNPG and 0.35 g (79.5 wt % of total DBNPG and TBNPA weight in the toluene layer) of TBNPA. This represents 87.5 wt % of the starting TBNPA and 2.4 wt % of the starting DBNPG.

EXAMPLE II

The same procedure of Example I was followed except that 50.0 g of the Dow Chemical Company's FR-1138 ® flame retardant was used instead of the 5 g of material fed in Example I. The FR-1138 ® flame retardant contained 2.0 g (4.0 wt %) MBP, 43.5 g (87 wt %) DBNPG and 4.5 g (9 wt %) TBNPA. The solvent system comprised 100 mL of water and toluene in a 1:1 volume ratio. The resultant slurry was stirred for 2 hrs at 28° C. A snow-white solid powder was recovered by filtration and dried. This powder weighed 42.14 g and contained 0.34 g (0.08 wt %) MBP, 40.60 g (96 wt %) DBNPG and 1.27 g (3 wt %) TBNPA. The toluene layer contained 0.07 g of MBP, 0.65 g of DBNPG and 3.55 g of TBNPA. The water layer contained 1.44 g of MBP, 1.07 g of DBNPG and 0.04 g of TBNPA. The solids recovery was 84.3 wt % yield based upon the original amount of FR-1138 ® flame retardant fed. On the wt % basis of the total MBP, DBNPG and TBNPA in each layer, the toluene layer contained 1.6 wt % MBP, 15.2 wt % DBNPG and 83.2 wt % TBNPA, and the water layer contained 56.5 wt % MBP, 42 wt % DBNPG and 1.5 wt % TBNPA.

The monobromopentaerythritol (MBP), the dibromoneopentyl glycol (DBNPG) and the tribromoneopentyl alcohol (TBNPA) referred to herein can also be referred to as, respectively, 2-(bromomethyl)-2(hydroxymethyl)-1,3-propanediol, 2,2-bis(-bromomethyl)-1,3-propanediol, and 3-bromo-2,2-bis(-bromomethyl)-1-propanol.

What is claimed:

1. A process for treating a first product which contains monobromopentaerythritol, dibromoneopentyl glycol and tribromoneopentyl alcohol to yield a second product having a dibromoneopentyl glycol content, on a weight percent basis, greater than that of said first product, said process comprising:
    a. forming a stirrable mass from at least (i) said first product and (ii) a solvent system in which, at a temperature within the range of from about 0° C. to about 40° C., said monobromopentaerythritol and said tribromoneopentyl alcohol are more soluble than said dibromoneopentyl glycol and in which at least 85% of said dibromoneopentyl glycol in said mass is insoluble;
    b. maintaining said mass at said temperature whereby said mass comprises (i) an insoluble portion and (ii) a solvent and solute portion; and
    c. separating said insoluble portion and said solvent and solute portion without the substantial precipitation of the solute from said solvent and solute portion, said separated insoluble portion being said second product.

2. The process of claim 1 wherein said first product is prepared by the bromination of pentaerythritol with HBr in the presence of an acid catalyst.

3. The process of claim 1 wherein said solvent system is comprised of a first solvent and a second solvent, said first and second solvents being immiscible in one another, said first solvent preferentially solubilizing said monobromopentaerythritol and said second solvent preferentially solubilizing said tribromoneopentyl alcohol and wherein said solvent and solute portion is comprised of two parts, the first part containing said first solvent and its solutes and a second part containing said second solvent and its solutes.

4. The process of claim 3 wherein said first solvent is water and said second solvent is toluene.

5. The process of claim 4 wherein volume ratio of said water to said toluene is within the range of from about 0.1:1 to about 1:0.1.

6. The process of claim 4 wherein said water is present in an amount of from about 1 to about 2 mL/g of said first product in said reaction mass.

7. The process of claim 1 wherein said mass, prior to (b), is brought to a temperature within the range of from about 25° C. to about 75° C.

8. A process for treating a first product which contains monobromopentaerythritol, dibromoneopentyl glycol and tribromoneopentyl alcohol to yield a second product having a monobromopentaerythritol content, on a weight percent basis, greater than that of said first product, said process comprising:
   a. forming a stirrable mass from at least (i) said first product and (ii) a solvent system in which, at a temperature within the range of from about 0° C. to about 40° C., said monobromopentaerythritol and said tribromoneopentyl alcohol are more soluble than said dibromoneopentyl glycol and in which at least 85% of said dibromoneopentyl glycol in said mass is insoluble, said solvent system being comprised of a first solvent and a second solvent, said first solvent and said second solvent being immiscible in one another, said first solvent preferentially solubilizing said monobromopentaerythritol and said second solvent preferentially solubilizing said tribromoneopentyl alcohol;
   b. maintaining said mass at said temperature whereby said mass comprises (i) an insoluble portion and (ii) a solvent and solute portion, said solvent and solute portion being comprised of two parts, a first part containing said first solvent and its solutes and a second part containing said second solvent and its solutes;
   c. separating said first part from said second part; and
   d. evaporating at least a part of said first solvent from said first part to form a precipitate containing monobromopentaerythritol, said precipitate being said second product.

9. A process for treating a first product which contains monobromopentaerythritol, dibromoneopentyl glycol and tribromoneopentyl alcohol to yield a second product having a tribromoneopentyl alcohol content, on a weight percent basis, greater than that of said first product, said process comprising:
   a. forming a stirrable mass from at least (i) said first product and (ii) a solvent system in which, at a temperature within the range of from about 0° C. to about 40° C., said monobromopentaerythritol and said tribromoneopentyl alcohol are more soluble than said dibromoneopentyl glycol and in which at least 85% of said dibromoneopentyl glycol in said mass is insoluble, said solvent system being comprised of a first solvent and a second solvent, said first solvent and said second solvent being immiscible in one another, said first solvent preferentially solubilizing said monobromopentaerythritol and said second solvent preferentially solubilizing said tribromoneopentyl alcohol;
   b. maintaining said mass at said temperature whereby said mass comprises (i) an insoluble portion and (ii) a solvent and solute portion, said solvent and solute portion being comprised of two parts, a first part containing said first solvent and its solutes and a second part containing said second solvent and its solutes;
   c. separating said second part from said first part; and
   d. evaporating at least a part of said second solvent from said second part to form a precipitate containing tribromoneopentyl alcohol, said precipitate being said second product.

* * * * *